(12) United States Patent
Lorenz et al.

(10) Patent No.: US 6,876,931 B2
(45) Date of Patent: Apr. 5, 2005

(54) AUTOMATIC PROCESS FOR SAMPLE SELECTION DURING MULTIVARIATE CALIBRATION

(75) Inventors: Alexander D. Lorenz, Phoenix, AZ (US); Timothy L. Ruchti, Gilbert, AZ (US); Thomas B. Blank, Chandler, AZ (US)

(73) Assignee: Sensys Medical Inc., Chandler, AZ (US)

( * ) Notice: Subject to any disclaimer, the term of this patent is extended or adjusted under 35 U.S.C. 154(b) by 185 days.

(21) Appl. No.: 10/211,142

(22) Filed: Aug. 2, 2002

(65) Prior Publication Data

US 2003/0109998 A1 Jun. 12, 2003

Related U.S. Application Data

(60) Provisional application No. 60/310,033, filed on Aug. 3, 2001.

(51) Int. Cl.$^7$ .............................................. G01N 31/00
(52) U.S. Cl. ....................................................... 702/22
(58) Field of Search ............................ 702/22, 23, 75, 702/76, 106; 600/316, 310, 322; 128/633

(56) References Cited

U.S. PATENT DOCUMENTS

| | | | | |
|---|---|---|---|---|
| 5,857,462 A | * | 1/1999 | Thomas et al. ............. | 600/310 |
| 6,134,458 A | * | 10/2000 | Rosenthal .................... | 600/310 |
| 6,135,965 A | * | 10/2000 | Tumer et al. ................ | 600/476 |
| 6,280,381 B1 | * | 8/2001 | Malin et al. ................. | 600/322 |

* cited by examiner

Primary Examiner—Edward Raymond
(74) Attorney, Agent, or Firm—Glenn Patent Group; Michael A. Glenn

(57) ABSTRACT

A process for enhancing a multivariate calibration through optimization of a calibration data set operates on a large calibration set of samples that includes measurements and associated reference values to automatically select an optimal sub-set of samples that enables calculation of an optimized calibration model. The process is automatic and bases sample selection on two basic criteria: enhancement of correlation between a partner variable extracted from the independent variable and the dependent variable and reduction of correlation between the dependent variable and interference. The method includes two fundamental steps: evaluation, assigning a measurement of calibration suitability to a subset of data; and optimization, selecting an optimal subset of data as directed by the measurement of suitability. The process is particularly applied in enhancing and automating the calibration process for non-invasive measurement glucose measurement but can be applied in any system involving the calculation of multivariate models from empirical data sets.

63 Claims, 3 Drawing Sheets

AUTOMATIC PROCESS FOR SAMPLE SELECTION DURING MULTIVARIATE CALIBRATION

CROSS-REFERENCE TO RELATED APPLICATION

This application claims benefit of U.S. Provisional Patent Application Ser. No. 60/310,033, filed on Aug. 3, 2001.

BACKGROUND OF THE INVENTION

1. Field of the Invention

The present invention relates to the development of optimized multivariate models through a calibration set of empirical data. More particularly, the present invention relates to the automatic selection of a data sub-set from a larger set of potential calibration data that provides improved performance (accuracy) and robustness.

2. Description of Related Technology

In general, near-infrared (NIR) diffuse reflectance spectroscopy involves the illumination of a spot on the body with low energy near-infrared light (700–2500 nm). The light is partially absorbed and scattered, according to its interaction with chemical components within the tissue, prior to being reflected back to a detector. The absorbance of light at each wavelength is a function of the structural properties and chemical composition of the tissue. Tissue layers, each containing a unique heterogeneous particulate distribution, affects light absorbance through scattering. Chemical components such as water, protein, fat, and analytes absorb light proportionally to their concentration through unique absorption profiles or signatures. The measurement of glucose is based on detecting the magnitude of light scatter and attenuation related to its concentration as spectrally manifested through the use of a calibration.

A calibration is a mathematical model, $g(?)$, that relates a set of M independent variables, $x \in \Re^{M \times 1}$, to a dependent variable, y through $$\hat{y} = g(x)$$

where $\hat{y}$ is an estimate of the dependent variable. In the linear case, $$\hat{y} = xG + b$$

where $G \in \Re^{M \times 1}$ is a regression vector and b is an offset. The process of calibration involves the determination of $g(?)$ on the basis of an exemplary set of N paired data points or samples, called the "calibration set". Each sample consists of a measurement of the independent variable, x, and an associated measurement of a dependent variable, y. The method for designing the structure of $g(?)$ is through the process of system of identification [L. Ljung, *Systems Identification: Theory for the User*, 2d.ed., Prentice Hall (1999)]. The model parameters are calculated using known methods including multivariate regression or weighted multivariate regression [N. Draper, H. Smith, *Applied Regression Analysis*, 2d.ed., John Wiley and Sons, New York (1981)], principal component regression [H. Martens, T. Naes, *Multivariate Calibration*, John Wiley and Sons, New York (1989)], partial least squares regression [P. Geladi, B. Kowalski, *Partial least-squares regression: a tutorial*, Analytica Chimica Acta, 185, pp.1–17, (1986)], or artificial neural networks [S. Haykin, *Neural Networks: A Comprehensive Foundation*, Prentice Hall, Upper Saddle River N.J. (1994)].

As indicated above, a primary use of a calibration is for the estimation of a dependent variable on the basis of an independent measurement. In the case of the non-invasive measurement of glucose through near-infrared spectroscopy, the dependent variable is the subject's glucose concentration and the independent variable is a near-infrared spectrum, after suitable processing. However, the use of calibrations is not limited to non-invasive measurement of glucose but, rather, applies to any application in which an indirect measurement of a property value (dependent variable) is required on the basis of more than one independent variable.

The design and collection of the calibration set is of great importance because the performance of the resulting model is intimately linked to the quality of the calibration data [see, for example, T. Isaksson, T. Naes, *Selection of samples for calibration in near-infrared spectroscopy. Part I: general prinicples illustrated by example*, Applied Spectroscopy, Vol. 43, No. 2, pp. 328–335, 1989 and T. Isaksson and T. Naes, *Selection of samples for calibration in near-*infrared *spectroscopy. Part II: selection based on spectral measurements*, Applied Spectroscopy, Vol. 44, No. 7, pp. 1152–1158, 1990]. A minimal requirement is that the data in the calibration set must comprehensively represent the potential variation in x and y. However, this criterion does not guarantee a calibration set will be sufficient. In particular, two significant problems related to the calibration set can adversely effect the determination of $g(?)$. First, individual paired data points can contain errors in x or y as a result of measurement error, poor instrument performance and other anomalies. Such data points, often referred to as "outliers", should be removed to avoid a poor estimate of $g(?)$.

Second, interfering variables or constituents in x that are present at the time of data collection introduce the potential for unintended or ancillary correlations between the dependent variable and other unrelated variables. If this correlation is manifested in x and is consistent throughout the calibration set, a false calibration will result that fails when this correlation is absent. In the case of noninvasive glucose measurement, the potential for false correlations is a consequence of the complexity of the sample and the measurement process [see M. Arnold, J. Burmeister, G. Small, *Phantom glucose calibration models from simulated noninvasive human near-infrared spectra*, Analytical Chemistry, vol. 70:9, pp. 1773–1771 (May 1, 1998)]. The multifaceted matrix of blood and tissue constituents introduces the potential for unintended correlations between glucose and other analytes.

In addition, the glucose levels of subjects may move relatively slowly throughout the course of a data collection period and may correspond consistently with other variables such as time, sample order, instrument drift, room temperature, patient skin temperature and skin hydration. Therefore, experimental conditions can lead to spectral aberrations that fortuitously vary consistently with glucose. Models based on data containing fortuitous and spurious correlations between glucose and other variables are erroneous and therefore not suitable for directing insulin therapy in diabetics.

Therefore, the creation of a suitable calibration set is generally performed on the basis of an experimental design and subsequent execution of the experiment [see H. Martens, T. Naes, *Multivariate Calibration*, John Wiley and Sons, New York (1989)]. However, there are often circumstances that prohibit a comprehensive experimental design and/or involve uncontrollable samples. For example, when the target apparatus involves the measurement of an attribute of a biological system, such as near-infrared measurement of glucose in humans, absolute control of the diversity of factors affecting calibration is difficult. As reported by S. Malin, T. Ruchti, An Intelligent System for Noninvasive Blood Analyte Prediction, U.S. Pat. No. 6,280,381 (Aug. 28, 2001), commonly-owned with the current application, uncontrollable chemical, structural, and physiological variations occur in tissue that produce dramatic and nonlinear changes in the optical properties of the tissue sample.

In such circumstances, an additional step of selecting a suitable subset of calibration data from a larger data is desirable. Several methods have been reported that base the selection of a calibration subset on the basis of the independent variable [see, for example D. E. Honigs, G. M. Hieftje, H. L. Mark and T. B. Hirschfeld, *Unique-Sample Selection via Near-Infrared Spectral Subtraction, Analytical Chemistry*, Vol. 57, No. 12, pp. 2299–2303, 1985; E. Bouveresse, C. Harmn, D. L. Massart, I. R. Last, and K. A. Prebble, *Analytical Chemistry*, Vol. 68, pp. 982–990, 1996; and Isaksson, et al., supra (1)]. Such methods fail to make use of the dependent variables and do not guarantee to produce unbiased models. In addition, the problem of fortuitous correlations remains unaddressed in these reports.

J. M. Brown, Method for optimizing multivariate calibrations, U.S. Pat. No. 6,233,133 (Apr. 24, 2001) describes a method for selecting a subset of samples for calibration on the basis of a larger set to minimize the bias in the y-block while ensuring that the x-block range is adequately spanned by the calibration set. However, the method fails to address the problem of ancillary correlations that, in certain applications, are pervasive within the larger data set. In addition, the method of selection is undirected and based upon a fitness function that depends upon the results from a calibration model that is calculated for each potential subset. Consequently, the results may vary significantly on the basis of the method of calibration and the determination of the suitable rank of the calibration model.

Fundamentally, no method has been reported to automatically select calibration samples that minimizes the potential for a calibration model that includes spurious correlations. In addition, no automated process has been designed to enhance the accessibility of the target signal within the calibration set while minimizing the correlation to interfering variables. Finally, no method has been reported that automatically identifies and removes invalid samples from a calibration set.

In view of the problems left unsolved by the prior art, there exists a need for a method to optimize the calibration set in a manner that reduces the likelihood of spurious correlations. Further, it would be beneficial to provide a method of selecting calibration samples that enables the efficient extraction of the target signal. Finally, it would be a significant advancement if the method were automatic and, as part of its operation, removed invalid samples.

SUMMARY OF THE INVENTION

The invention provides a process for enhancing a multivariate calibration through improved design of a calibration data set. The process of the invention operates on a large calibration set of samples consisting of measurements, x, and associated reference values, y, to automatically select an optimal or near-optimal sub-set of samples that will lead to the determination or calculation of an improved calibration model. The general methodology for sample selection is based on maximizing the causal variation represented in the measurement, x, over the calibration set that is related to the target variable, y while reducing the correlation between y and unrelated variables. The process is automatic and bases sample selection on two basic criteria:

enhancement of the correlation between a partner variable or feature extracted from the independent variable and the dependent variable; and the reduction of the correlation between the dependent variable and interference.

In addition, the process can be performed with both criteria or with either criterion singly for the improvement of the calibration set.

The method includes two fundamental steps:

evaluation; and optimization.

Evaluation is a method for assigning a measurement of calibration suitability, herein referred to as a figure of merit, to a particular subset of data. The means of evaluation may take the form of a fitness or cost function that provides a figure of merit associated with a subset of data or with each individual sample. The figure of merit represents (positively) at least the presence of the analytical signal and (negatively) the existence of a correlation to ancillary variables. In addition, the range of the dependent and independent variables, the spectral variation and number of samples can be included in the function.

Subsequently, a method of optimization selects an optimal or near-optimal subset of data as directed by the cost function or figure of merit. The invention provides several examples of an iterative approach to optimization. However, one skilled in the art will recognize that other methods of optimization are applicable including, for example, genetic algorithms [see Goldberg, D. E., *Genetic Algorithms in Search, Optimization and Machine Learning*, Addison Wesley Publishing Company, 1989].

The following process is explained specifically for application to calibration of a near-infrared spectrometer for noninvasive glucose measurement. However, one skilled in the art will recognize that this process is applicable to any instrument and any target analyte or variable.

While the invention ideally finds application in enhancing and automating the calibration process for the non-invasive measurement of glucose as disclosed in S. Malin, T. Ruchti, An Intelligent System for Noninvasive Blood Analyte Prediction, U.S. Pat. No. 6,280,381 (Aug. 28, 2001); and T. Ruchti, S. Thennadil, T. Blank, A. Lorenz, S. Monfre, Noninvasive measurement of glucose through the optical properties of tissue, PCT Application No. US02/02288, filed on Jan. 25, 2002, the entireties of which are hereby incorporated by reference, one skilled in the art will appreciate that the invention can be applied in any system involving the calculation of multivariate models from empirical data sets.

DETAILED DESCRIPTION

Evaluation

Figure 1:
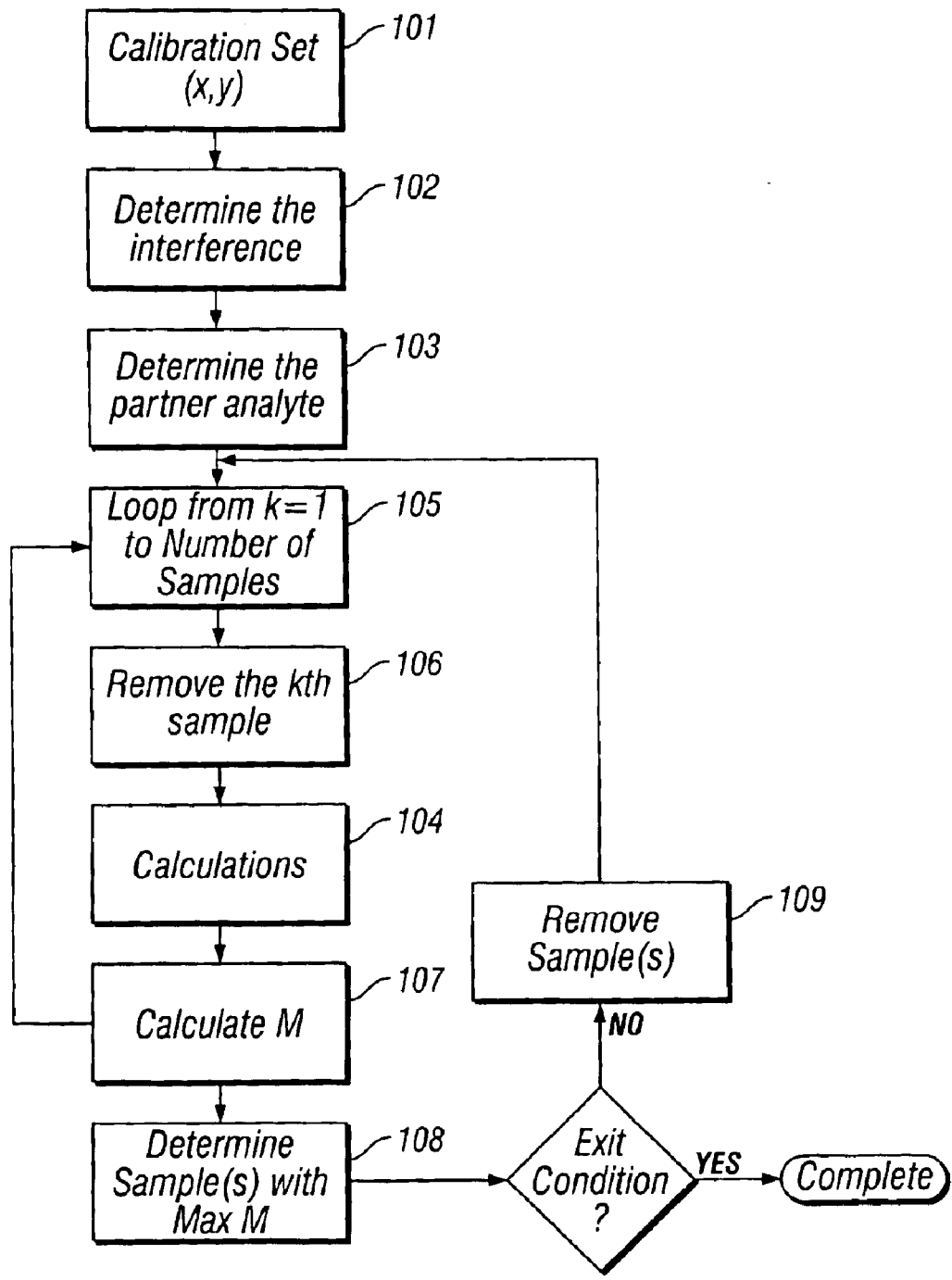
FIG. 1 provides a flow diagram of a preferred embodiment of an automated method for optimizing a calibration set according to the invention.

The invention utilizes either a figure of merit or a cost function for determining the quality of a particular subset of calibration samples. The basic elements of the cost function include:

a measure of the quality or magnitude of the accessible net analyte signal; and a measure of the lack of correlation between the dependent variable and ancillary or interfering variables, manifested in x, that correlate to y.

In addition, the cost function may optionally include any of:

the standard error of calibration;

the standard error of a monitoring or test set;

the range of the dependent variable;

the number of selected samples;

the total variation of the x-block; and other parameters that are indicative of a "good" calibration set.

In one implementation, the cost function involves the assignment of a cost or performance measurement for an overall set. For example, the cost function can be written $$J = \sum_{k=1}^{m} \alpha_k J_k(x_s, y_s) \quad (1)$$

where J is the cost associated with a particular subset of samples, $J_k(x,y)$ represents the kth cost associated with the sub-set of samples represented by the matrices $x_s$ and $y_s$, and $\alpha_k$ represents the weight or emphasis associated with the kth figure of merit. In an alternate implementation, an individual cost is computed for each sample that is present within a particular subset according to $$J_p = \sum_{k=1}^{m} \alpha_k J_{k,p}(x_p, y_p) \quad (2)$$

where $J_p$ is the cost associated with the pth sample, $\alpha_k$ represents the weight associated with the kth cost function, $J_{k,p}(x_p,y_p)$ represents the kth sub-cost function associated with sample s, and m represents the total number of sub-cost functions. The overall cost is the summation of the individual figures of merit associated with the samples of a particular subset.

Optimization

Optimization of the calibration set involves the determination of the subset of data that either minimizes a cost function or maximizes a figure of merit. In one embodiment, the process is performed in an iterative manner, beginning with the set of all samples. The cost of each sample or the combination of m samples is used at each iteration to remove one or more samples until a particular level of performance is achieved. Under this framework, hard inclusion and exclusion limits can be set to the final cost of each sample such that they are either included or excluded from the calibration set. Where it is possible for decisions to be made in an ordered manner according to a preset priority, a set of decision rules can be established in a hierarchical framework in which each individual cost or figure of merit is applied separately and in a particular order. Alternately, the calibration subset can begin with one or more samples and the cost function can be used to iteratively determine which sample, or combination of several samples, will lead to an improvement in overall performance. The process of adding one or more samples into the calibration set continues until a desired performance level is achieved.

Finally, the cost function can be optimized by global search techniques such as dynamic programming [Bellman, R. E. *Dynamic Programming*, Princeton University Press, Princetone, N.J., USA, 1957.], gradient search techniques [Gill, P. E., W. Murray and M. H. Wright, *Practical Optimization*, Academic Press, 1981.], random search techniques, genetic algorithms [Goldberg, D. E., *Genetic Algorithm in Search, Optimization and Machine Learning*, Addison Wesley Publishing Company, 1989.], or evolutionary programming [Fogel, D. B. *An Introduction to Simulated Evolutionary Optimization, IEEE Trans. On Neural Networks*, vol. 5, no. 1, January 1994.]. Given a cost function or method of evaluation as described previously, the sub-set of optimal or near-optimal samples are selected by application of any of these methods.

A genetic algorithm may be employed to select that sub-set from a set of samples that produces the best performance as indicated by the method of evaluation. The process involves the following steps:

1. initialization—creation of one or more populations of possible solutions. Each solution is a "chromosome" or a vector in which each element represent a sample. Therefore, each solution defines a set of calibration samples;

2. evaluation of each solution and the assignment of a measure of fitness according to the cost function or figure of merit;

3. selection of solutions in a random manner according to a probability related to the level of fitness;

4. reproduction—the randomized combination of various solutions to form a new population of possible solutions;

5. mutation—the random removal of samples from or the introduction of new samples into various solutions;

6. optionally, when multiple populations are employed, various solutions from each population are exchanged to enhance the diversity of each population; and 7. repeat Steps 2–5 until a target level of performance is achieved or the population(s) of solutions converges.

Preferred Embodiment

The preferred embodiment of the invention evaluates each sample and iteratively removes samples from the data set to enhance the overall performance. This process continues until a particular level of performance is achieved. The process is shown through a block diagram in FIG. 1 and consists of these general steps.

1. Collect Data (101)

Data is collected in paired data points each consisting of a measurement of the independent variable(s), x, and a target or dependent variable, y, from a reference device. For example, x can consist of a set of tissue absorbance spectra collected on a near-infrared spectrometer and y can be the set of corresponding glucose measurements taken on a Yellow Springs Instruments glucose analyzer. The data set, consisting of a N-by-M matrix, $\bar{x}$ and an N-by-1 matrix, $\bar{y}$, is termed the "calibration set" and is used in multivariate calibration to determine a model for calculating future analyte values, ŷ, given future device measurements.

2. Calculate Partner Variable (103)

The N-by-P partner variable, $\bar{z}$, is determined from the independent variable, $\bar{x}$, and is either the net analyte signal or is a feature related to the net analyte signal (NAS). The net analyte signal is the part of $\bar{x}$ that relates uniquely to $\bar{y}$ and is determined through a previously calculated calibration model [see A. Lorber, K. Faber, B. Kowalski, *Net analyte signal calculation in multivariate calibration, Analytical Chemistry*, vol. 69, pp. 1620–1626 (1997)]. Note that one or more partner variables can be defined when a multiplicity of prior calibrations exist or when more than one feature is required to reflect the net analyte signal. When a prior calibration model exists in the form of a regression vector, $\bar{w}$, then $\bar{z}=\bar{x}\bar{w}$. When a calibration does not exist but a feature is known that reflects the net analyte signal present in $\bar{x}$ then it is used by itself or in combination with other features as $\bar{z}$. For example, in the application of noninvasive glucose measurement the critical points of the first and second derivative from the measured near-infrared spectrum are valuable features related to the net analyte signal of glucose.

In one embodiment of the invention, the absorbance spectra of water, fat and/or protein are used as features related to the net analyte signal. The features are resolved by calculating the first or second derivative of each spectrum and determining the magnitude at the appropriate wavelengths (e.g. the following wavelengths ±1–5 nm: 1095, 1125, 1155, 1180, 1200, 1308, 1338, 1380, 1414, 1443, 1458, 1550, 1593, 1607, 1625, 1661, 1687, 1706, 1727, 1747, 1783, 1874, 1784, 1910). These wavelengths are disclosed because variations that are consistently related to glucose can be detected through the absorbance spectrum, the first derivative absorbance spectrum and second derivative absorbance spectrum at or near these wavelengths.

Further methods for determining partner analytes in the form of physiological variation that is consistently related to a particular analyte have been previously described in Ruchti, et al., supra.

In the preferred embodiment, the regression vector from another subject, a variety of subjects or a group of subjects is used to determine P estimates of the net analyte signal present in each row of $\bar{x}$.

3. Determine the Interference (102)

The interference is any variable other than the dependent variable that is manifested in the independent variable (after processing and feature extraction) that may correlate with the target variable over time. For noninvasive glucose measurement the following interferences have been identified:

a. Environmental temperature
 b. Instrument temperature
 c. Sample temperature
 d. Absolute humidity
 e. Instrument drift
 f. Time (sample order)
 g. Sample parameters: hydration, surface water, skin thickness, blood content in tissues, hematocrit concentration, trigylceride concentration, sodium levels, cholesterol levels, surface hydration, blood pressure, and tissue pH.

In the preferred embodiment, one or more of the variables above are contained in the vector $\bar{b}$ and are identified as the interference.

4. Determine the Inaccessible Portion of the Target Variable (104)

Determine the inaccessible portion of the target variable, $\bar{y}$, by projecting it onto the null space of the partner variables through $$nas_{noise}=\|(I-\bar{z}\bar{z}^+)\bar{y}\|$$

where 51 is the identity matrix, $\bar{z}^+$ is the pseudo inverse of $\bar{z}$ given by $(\bar{z}'\bar{z})^{-1}\bar{z}'$ and $\|?\|$ is the norm. The scalar $nas_{noise}$ is an estimate of the variance in $\bar{y}$ that is not represented in $\bar{z}$. Reasons for higher values of $nas_{noise}$ include poor sample reproducibly, noise and interference.

5. Determine the Accessible Portion of the Analyte (104)

Determine the accessible portion of the analyte, given the interference, according to $$nas_{signal}=\|(I-\bar{b}\bar{b}^+)\bar{y}\|$$

The scalar $nas_{signal}$ is an estimate of the independence of the analyte values from the interference or the information that can be accessed in the presence of the interference. When spurious correlations are present in the data a net reduction in $nas_{signal}$ is detected.

6. Estimate the Signal-to-Noise Ratio (SNR) (104)

Estimate SNR:

$$SNR = \frac{nas_{signal}}{nas_{noise}}.$$

7. Estimate Correlation Coefficient Between $nas_{signal}$ and $\bar{z}$ (104)

Estimate R, the correlation coefficient between $nas_{signal}$ and $\bar{z}$ (if $\bar{z}$ has been more than one column, R is the minimum correlation coefficient between the columns of $\bar{z}$ and $nas_{signal}$).

8. Iteratively Perform Steps 2–7 (105)

Iteratively perform steps 2–7 106 leaving one of the samples out (106) at each iteration. The result will be N-dimensional vectors for $\overline{SNR}$, $\overline{nas}_{signal}$, $\overline{nas}_{noise}$ and $\bar{R}$ corresponding to the respective calculation when each particular given sample is removed.

9. Select Sample to Remove (107, 108)

The sample to remove is selected as the one that maximizes the N-by-1 goodness measure $\bar{M}$ where $\bar{M}$ is a combination of one or more of the following:

a. $\overline{SNR}$
 b. $\bar{R}^2$ (squared element-by-element)
 c. $\bar{R}^2\,\overline{SNR}$
 d. $\overline{nas}_{signal}$ In the preferred embodiment limits are set for the minimum value of $\overline{nas}_{signal}$ and the maximum value for $\overline{nas}_{noise}$, denoted $c_{signal}$ and $c_{noise}$ respectively. The goodness measure is determined 107 as follows:

---

If $nas_{signal,k-1} < c_{signal}$ and $nas_{noise,k-1} > c_{noise}$ then
  $\bar{M} = \bar{R}^2\overline{SNR}$
else if $nas_{signal,k-1} > c_{signal}$ and $nas_{noise,k-1} > c_{noise}$ then
  $\bar{M} = \overline{nas}_{signal}$
else
  $\bar{M} = \bar{R}^2$
end

--- where $nas_{signal,k-1}$ and $nas_{noise,k-1}$ refer to the final $nas_{signal}$ and $nas_{noise}$ from the prior iteration. Alternately, $\bar{M}$ is given by $$\bar{M}=a_1\bar{R}^2+a_2\overline{SNR}+a_3\overline{nas}_{signal}$$

where $a_k$ are coefficients. The sample selected for removal corresponds to the element of $\bar{M}$ with the maximum value 108). Note that the criteria above can be modified according to the information that is available. When a partner analyte is not available then $a_2=0$ and the criteria above is used to reduce the correlation and magnitude of the interference. Alternately, if measures of interference are not accessible, then $a_1=0$ and $a_3=0$ and SNR is replace with $nas_{noise}$.

10. Steps 2–9 Continue (109)

Steps 2–9 continue until the target values for $c_{signal}$ and $c_{noise}$ are obtained, a desired number of samples are removed the maximum number of samples are removed, or removal of further samples would fail to produce a statistically significant increase in $\bar{M}$ through an F-test of $\max(\bar{M})$ versus $\max(\bar{M}_{k-1})$.

At the conclusion of the sample selection process, the samples are evaluated to determine if $c_{signal}$ and $c_{noise}$ have been obtained. If they have, then the measurement data are preprocessed and a calibration is automatically calculated using known methods including any of: linear regression, multiple linear regression, principal component regression, partial least squares regression, artificial neural networks or other method for calibration determination.

Several versions of current embodiment of the invention have been developed by modifying the manner in which samples are left out during for the calculation of $\overline{M}$. In one version, groups of samples are left out at each iteration, either ordered by sample or randomly selected. Alternately, $\overline{M}$ can be determined by iteratively removing samples and iteratively putting previously removed samples back into the calculation. In this embodiment samples can be removed and put back into the final calibration set.

Other methods of optimization are readily applicable. For example, M can be calculated for every possible combination of the N samples or every possible combination of j samples where j is the desired number of samples in the final data set. The final calibration set is selected as the one associated with the highest value for M. In applications with many samples genetic algorithms or simulated annealing are applied to optimize M.

Alternate Embodiment

Figure 2:
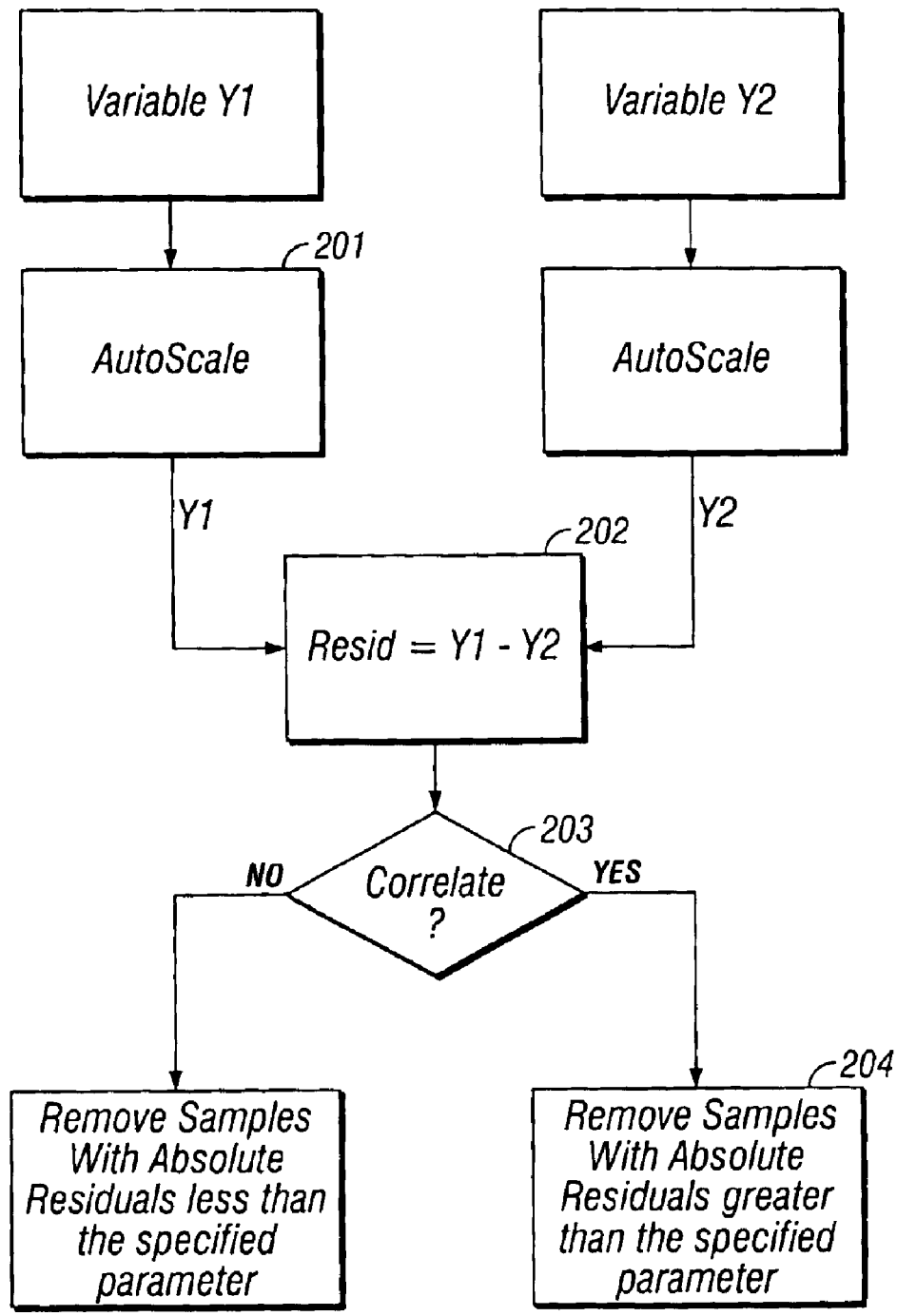
FIG. 2 diagrams an alternate embodiment of the method of FIG. 1.

An alternate embodiment, shown in FIG. 2, includes or excludes samples on the basis of correlation to ancillary parameters. These parameters may be computed from the spectral measurement, x, or captured from external instrumentation such as a temperature probe. Ancillary variation that is consistent with the NAS can be used to the screen data for samples that contain a strong signal. Therefore, if the parameter is related to the NAS, this method will select samples to include such that the correlation is increased. Conversely if a parameter is destructive and non-related to the NAS, it will select samples to exclude such that the correlation is decreased. This method allows constructive samples to positively influence the estimation of the NAS and restricts destructive samples from impeding the estimation of the NAS. The first step is to scale 202 the property values of both the signal being regressed and targeted ancillary parameter to mean zero and unit variance. The expression for this step is:

$$X = \frac{x - \bar{x}}{\sigma_x}$$

where X is the variance scaled data points, x is the measured or computed property values, $\bar{x}$ is the mean of the x, and $\sigma_x$ is the standard deviation of x. The next step is to compute a difference between the two by subtracting one data set from the other 202.

The residuals are compared to specified parameter 203. The last step 204 is then to remove samples with absolute residuals greater or less than a specified parameter in order to increase or decrease the correlation to the target parameter respectively.

Figure 3:
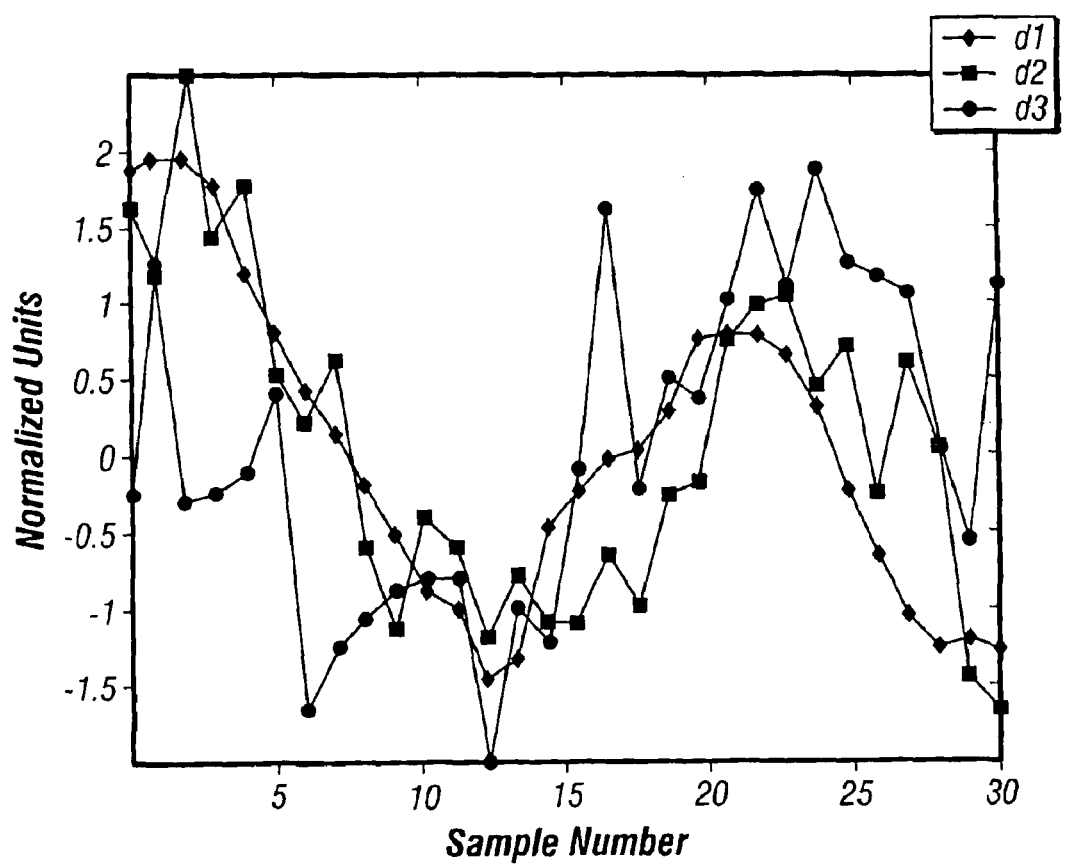
FIG. 3 shows a plot of data sets used to validate the embodiment of FIG. 2 according to the invention.

To demonstrate this method, three data sets containing 30 values each will be used. The first data set (d1) represents the property value that is being modeled. The second data set (d2) represents an ancillary parameter that is related to the NAS, and the last data set (d3) represents an ancillary parameter that is destructive to the NAS. FIG. 3 displays the variance scaled data sets. The methodology defined above was applied to data sets d1 and d2 to increase the correlation. It was then applied to data sets d1 and d3 to decrease the correlation. Table 1, below, displays the results before and after data selection and which samples were removed to achieve the respected correlation. The parameter for selection/rejection was set to 0.5

TABLE 1

| Data set | R before | R after | Samples removed |
|---|---|---|---|
| d2 | .81 | .96 | 2, 5, 10, 15–20, 25, 27–28 |
| d3 | .25 | −.05 | 6, 10–16, 18–21, 23 |

While this embodiment details the iterative evaluation and removal of single samples, an alternate implementation involves the iterative evaluation and removal of groups of samples. In this embodiment groups of two or more samples are evaluated together and removed as herein described.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A method for optimizing a calibration set comprising the steps of:

providing a calibration set of spectral samples and associated reference values;

assigning a measure of fitness for calibration to individual samples or subsets of samples from the calibration set according to a cost function; and determining a subset of samples having an optimal measure of fitness by creating new groupings of samples until a subset results that provides a target performance, wherein spurious variations are not correlated to a net analyte signal.

2. A method as in claim 1, wherein said cost function comprises a measure of the quality or magnitude of accessible net analyte signal.

3. A method as in claim 1, wherein said cost function comprises a measure of a lack of correlation between a dependent variable and ancillary or interfeting variables manifested in x, x representing at least one spectral sample, that correlates to y, y representing a reference value.

4. A method as in claim 1 wherein said cost function includes any of:

a standard error of calibration;

a standard error of a monitoring or test set;

range of a dependent variable, wherein the dependent variable comprises one or more of said reference values;

the number of selected samples;

the total variation of the x-block, wherein the x-block includes said spectral samples; and additional parameters that are indicative of an optimal calibration set.

5. A method as in claim 1, wherein the cost function involves the assignment of a cost or performance measurement for an overall set according to:

$$J = \sum_{k=1}^{m} \alpha_k J_k(x_s, y_s)$$

where J Is the cost associated with a particular subset of samples, $J_k(x,y)$ represents the $k^{th}$ cost associated with the subset of samples represented by $x_s$ and $y_s$, and $x_k$ represents the weight or emphasis associated with the $k^{th}$ figure of merit.

6. A method as in claim 1, wherein an individual cost is computed for each sample that is present within a particular subset according to:

$$J_p = \sum_{k=1}^{m} \alpha_k J_{k,p}(x_p, y_p)$$

where $J_p$ is the cost associated with the $p^{th}$ sample, $\alpha_k$ represents the weight associated with the $k^{th}$ cost function, $J_{k,p}(x_p, y_p)$ represents the $k^{th}$ sub-cost function associated with the sample.

7. A method as in claim 6, wherein m represents the total number of sub-cost functions.

8. A method as in claim 6, wherein the overall cost is the summation of the individual figures of merit associated with the samples of a particular subset.

9. A method as in claim 1, wherein determining a subset of samples having an optimal measure of fitness comprises determining a subset that either minimizes cost or maximized a figure of merit.

10. A method as in claim 1, wherein determining a subset of samples having an optimal measure of fitness is performed in an iterative manner.

11. A method as in claim 10, wherein determining a subset of samples having an optimal measure of fitness comprises using cost of each sample, or the cost of all samples is used at each iteration to remove at least one sample until said target level of performance is achieved.

12. A method as in claim 11, wherein hard inclusion and exclusion limits are set to the final cost of each sample so that they are either included in or excluded from the calibration set.

13. A method as in claim 11, wherein determining a subset of samples having an optimal measure of fitness comprises establishing a set of decision rules in a hierarchical framework in which each individual cost or figure of merit is applied separately and in a particular order.

14. A method as in claim 11, wherein determining a subset of samples having an optimal measure of fitness comprises:
  beginning with a subset that includes at least one sample; and
  iteratively adding one or more samples into the calibration set until a desired performance level is achieved.

15. A method as in claim 11, wherein determining a subset of samples having an optimal measure of fitness comprises selecting a subset of optimal or near optimal samples according to any of the techniques of:
  dynamic programming;
  gradient searching;
  random searching;
  genetic algorithms; and
  evolutionary programming.

16. A method as in claim 15, wherein determining a subset of samples having an optimal measure of fitness according to a genetic algorithm comprises performing the following steps iteratively until a target level of performance is achieved or until at least one population of solutions converges:
  creating one or more populations of possible solutions, wherein each solution is a "chromosome" or a vector in which each element represents a sample, so that each solution defines a set of calibration samples;
  evaluating each solution and assigning a measure of fitness according to the cost function;
  selecting solutions in a random manner according to a probability related to the level of fitness;
  randomly combining various solutions to form a new population of possible solutions;
  randomly removing samples from, or introducing new samples into various solutions; and
  optionally, when multiple populations are employed, exchanging various solutions from each population to enhance the diversity of each population.

17. A method as in claim 1, wherein providing a calibration set of spectral samples and associated reference values comprises:
  collecting data.

18. A method as in claim 17, wherein determining a subset of samples having an optimal measure of fitness comprises:
  A. calculating at least one partner variable;
  B. determining interference;
  C. determining an inaccessible portion, $c_{noise}$, of an analyte signal;
  D. determining an accessible portion, $c_{signal}$, of the analyte signal;
  E. estimating a signal-to-noise-ratio (SNR) according to:

$$SNR = \frac{nas_{signal}}{nas_{noise}};$$

F. estimating a correlation coefficient between said partner variable and the accessible portion of the analyte signal;
  G. iteratively performing steps A–F, leaving at least one sample out at each iteration;
  H. selecting a sample to remove; and
  I. continuing steps A–H until said target performance is achieved.

19. A method as in claim 18, wherein collecting data comprises collecting paired data points each consisting of a measurement of an independent variable(s), x, and a target or dependent variable, y, from a reference device.

20. A method as in claim 19, wherein x comprises at least one tissue absorbance spectrum collected on a near-infrared spectrometer and y comprises at least one corresponding glucose measurement taken on a glucose analyzer.

21. A method as in claim 20, wherein said calibration set comprises a N-by-M matrix, $\bar{x}$ and an N-by-1 matrix, $\bar{y}$;
  wherein said calibration set is used in multivariate calibration to determine a model for calculating future analyte values, $\bar{y}$, given future analyzer measurements.

22. A method as in claim 21, wherein step A comprises calculating an N-by-P partner variable, $\bar{z}$, from the independent variable, $\bar{x}$.

23. A method as in claim 22, wherein said partner variable is either the net analyte signal (NAS) or a feature related to the NAS.

24. A method as in claim 22, wherein the NAS is the part of $\bar{x}$ that relates uniquely to $\bar{y}$ and is determined through a previously calculated calibration model.

25. A method as in claim 22, wherein step A comprises defining one or more partner variables when a multiplicity of prior calibrations exist or when more than one feature is required to reflect the NAS.

26. A method as in claim 22, wherein $\bar{z}=\overline{xw}$ when a prior calibration model exists in the form of a regression vector, $\bar{w}$.

27. A method as in claim 26, wherein a regression vector from another subject, a variety of subjects or a group of subjects is used to determine P estimates of the net analyte signal present in each row of $\bar{x}$.

28. A method as in claim 22, wherein, if a feature is known that reflects the net analyte signal present in $\bar{x}$, said feature is used by itself or in combination with other features as $\bar{z}$ if a calibration does not exist.

29. A method as in claim 23, wherein critical points of first and second derivatives from said near-infrared spectrum are valuable features related to the NAS of glucose.

30. A method as in claim 29, wherein absorbance spectra of any of water, fat and protein are used as features related to the NAS.

31. A method as in claim 30, wherein said critical points are resolved by calculating the first or second derivative of each spectrum and determining the magnitude at the appropriate wavelengths.

32. A method as in claim 31, wherein the appropriate wavelengths include any of 1095±1–5 nm; 1125±1–5 nm; 1155±1–5 nm; 1180±1–5 nm; 1200±1–5 nm; 1308±1–5 nm; 1338±1–5 nm; 1380±1–5 nm; 1414±1–5 nm; 1443±1–5 nm; 1458±1–5 nm; 1550±1–5 nm; 1593±1–5 nm; 1607±1–5 nm; 1625±1–5 nm; 166±1–5 nm 1687±1–5 nm; 1706±1–5 nm; 1727±1–5 nm; 1747±1–5 nm; 1783±1–5 nm; 1874±1–5 nm; 1784±1–5 nm; and 1910±1–5 nm.

33. A method as in claim 22, wherein the interference is any variable other than the dependent variable that is manifested in the independent variable, after processing and feature extraction, that correlates with the target variable over time.

34. A method as in claim 33, wherein interference includes any of:

environmental temperature;

instrument temperature;

sample temperature;

absolute humidity;

instrument drift;

time or sample order; and sample parameters, wherein sample parameters include any of:

hydration, surface water, skin thickness, blood content in tissues, hematocrit concentration, trigylceride concentration, sodium levels, cholesterol levels, surface hydration, blood pressure, and tissue pH.

35. A method as in claim 33, wherein said variables other than the dependent variable are contained in a vector $\bar{b}$ and are identified as the interference.

36. A method as in claim 22, wherein $nas_{noise}$ is an estimate of the variance $\bar{y}$ that is not represented in $\bar{x}$.

37. A method as in claim 36, wherein $nas_{signal}$ is an estimate of the independence of the analyte values from the interference or the information that can be accessed in the presence of the interference.

38. A method as in claim 37, wherein step F comprises estimating R, the correlation coefficient between $nas_{signal}$ and $\bar{z}$.

39. A method as in claim 38, wherein, if $\bar{z}$ has been more than one column, R is the minimum correlation coefficient between the columns of $\bar{z}$ and $nas_{signal}$.

40. A method as in claim 38, wherein a result of step G comprises N-dimensional vectors for $\overline{SNR}$, $\overline{nas}_{signal}$, $\overline{nas}_{noise}$ and $\overline{K}$ corresponding to the respective calculation when each particular given sample is removed.

41. A method as in claim 40, wherein step H comprises selecting the sample to remove that maximizes the N-by-1 measure of fitness, $\overline{M}$, where $\overline{M}$ includes any of:

$\overline{SNR}$;

$\overline{R^2}$, squared element-by-element;

$\overline{R^2 SNR}$; and $\overline{nas}_{signal}$.

42. A method as in claim 41, wherein limits are set for the minimum value of $\overline{nas}_{signal}$ and the maximum value for $\overline{nas}_{noise}$, denoted $c_{signal}$ and $c_{noise}$ respectively.

43. A method as in claim 42, further comprising determining said measure of fitness according to:

If $nas_{signal,k-1} < c_{signal}$ and $nas_{noise,k-1} > c_{noise}$ then
$\overline{M} = \overline{R^2 SNR}$;
else if $nas_{signal,k-1} > c_{signal}$ and $nas_{noise,k-1} > c_{noise}$ then
$\overline{M} = nas_{signal}$;
else
$\overline{M} = \overline{R^2}$
end;

where $nas_{signal,k-1}$ and $nas_{noise,k-1}$ refer to the final $nas_{signal}$ and $nas_{noise}$ from the prior iteration.

44. A method as in claim 42, further comprising determining said measure of fitness according to:

$\overline{M} = a_1 \overline{R^2} + a_2 \overline{SNR} + a_3 \overline{nas}_{signal}$;

where $a_k$ are coefficients.

45. A method as in claim 44, wherein the sample selected for removal corresponds to the element of $\overline{M}$ having the maximum value.

46. A method as in claim 44, wherein criteria for modifying $\overline{M}$ are modifiable according to the information available.

47. A method as in claim 46, wherein $a_2 = 0$ when a partner analyte is not available.

48. A method as in claim 46, wherein, $a_1 = 0$, $a_3 = 0$ and SNR is replaced with $nas_{noise}$ if measures of interference are not accessible.

49. A method as in claim 41, wherein step I continues until target values for $c_{signal}$ and $c_{noise}$ are obtained.

50. A method as in claim 49, further comprising are preprocessing measurement data; and automatically calibrating a calibration using any of the methods of:

linear regression;

multiple linear regression;

principal component regression;

partial least squares regression; and artificial neural networks.

51. A method as in claim 41, wherein step I continues until a desired number of samples is removed.

52. A method as in claim 41, wherein step I continues until the maximum number of samples is removed.

53. A method as in claim 41, wherein step I continues until removal of further samples would fail to produce a statistically significant increase in $\overline{M}$ through an F-test of $\max(\overline{M})$ versus $\max(\overline{M}_{k-1})$.

54. A method as in claim 1, wherein creating new groupings of samples comprises iteratively leaving out groups of samples, said groups are either ordered by sample or randomly selected.

55. A method as in claim 1, wherein creating new groupings of samples comprises iteratively removing samples and iteratively putting previously removed samples back into the calculation.

56. A method as in claim 1, wherein a final calibration set is selected as the one associated having the highest value of said measure of fitness.

57. A method as in claim 1, wherein genetic algorithms or simulated annealing are applied to optimize said measure of fitness in applications with many samples.

58. A method as in claim 1, wherein determining a subset of samples comprises including or excluding samples on the basis of correlation to ancillary parameters.

59. A method as in claim 58, further comprising any of:
calculating said parameters from a spectral measurement, x; and
capturing said parameters from external instrumentation.

60. A method as in claim 59, wherein said external instrumentation comprises a temperature probe.

61. A method as in claim 58, further comprising scaling property values of both a signal being regressed, values of said signal comprising a first data set, and values of a targeted ancillary parameter, values of said parameter comprising a second data set, to mean zero and unit variance according to:

$$X = \frac{x - \bar{x}}{\sigma_x}$$

where X comprises variance scaled data points, x is measured or computed property values, $\bar{x}$ is the mean of x, and $\sigma_x$ is the standard deviation of x.

62. A method as in claim 61, further comprising computing a difference between the two data sets by subtracting one data set from the other.

63. A method as in claim 62, further comprising removing samples having absolute residuals greater or less than a specified parameter in order to increase or decrease the correlation to the target parameter.

* * * * *